United States Patent [19]

Buchel et al.

[11] 3,934,022
[45] Jan. 20, 1976

[54] N-TRITYL-IMIDAZOLES AS PLANT FUNGICIDES

[75] Inventors: Karl Heinz Buchel, Wuppertal-Elberfeld; Erik Regel, Wuppertal-Cronenberg; Ferdinand Grewe, Burscheid; Hans Scheinpflug; Helmut Kaspers, both of Leverkusen, all of Germany

[73] Assignee: Bayer Aktiengesellschaft, Germany

[22] Filed: Sept. 2, 1970

[21] Appl. No.: 69,110

Related U.S. Application Data

[62] Division of Ser. No. 789,601, Jan. 7, 1969, abandoned.

[30] Foreign Application Priority Data

Jan. 29, 1968 Germany............................ 1670976

[52] U.S. Cl. ............................................. 424/273
[51] Int. Cl.² ........................................ A01H 9/22
[58] Field of Search ................................ 424/273

[56] References Cited
UNITED STATES PATENTS 3,321,366   5/1967   Mussell et al. .................. 424/273

*Primary Examiner*—Jerome D. Goldberg

[57] ABSTRACT

Plant fungicidal compositions are produced which comprise an amount of a compound of the formula:

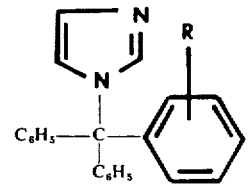

wherein R is alkyl of 1 to 3 carbon atoms, sufficient to be effective for killing, combatting or controlling plant fungi, in combination with a solid or liquid diluent or carrier. Methods for killing, combatting or controlling fungal diseases in plants comprise applying to the fungi or to the plant to be protected an effective or toxic amount of the above compound.

14 Claims, No Drawings

N-TRITYL-IMIDAZOLES AS PLANT FUNGICIDES

This is a division of our copending application Ser. No. 789,601, filed Jan. 7, 1969 now abandoned.

The present invention relates to and has for its objects the provision for particular new 1-[(halo, nitro, cyano, alkyl, alkyoxy, alkylmercapto and fluoro-alkyl-substituted phenyl)-(bis-phenyl)-methyl]-imidazoles, i.e., certain N-trityl-imidazoles, which possess fungicidal properties, active compositions in the form of mixtures of such compounds with solid and liquid dispersible carrier vehicles, and methods for producing such compounds and for using such compounds in a new way especially for combating fungi, with other and further objects becoming apparent from a study of the within specification and accompanying examples.

It is already known that N-tritylimidazoles of the general formula (i)

in which
X is an alkyl or aryl radical, and
R' is an aryl radical of the formula (ii)

in which
R'' is a halogen atom or a lower alkyl radical, and
n is 0, 1 or 2 compatibility
exhibit fungitoxic properties (compare U.S. Pat. No. 3,321,366).

However, no N-trityl-imidazoles of the formula (i) stated above are known in which X is always hydrogen and one of the radicals R' is substituted by R'' while the two other radicals R' have no substituents.

It has now been found, in accordance with the present invention, that the particular new N-trityl-imidazoles of the formula (I)

in which
R is halo, nitro, cyano, $C_{1-3}$ alkyl, $C_{1-3}$ alkoxy,
$C_{1-3}$ alkylmercapto or fluoro-substituted $C_{1-2}$ alkyl, exhibit strong fungicidal properties.

In our copending U.S. Application Ser. No. 789,602, filed Jan. 7, 1969, N-trityl-imidazolium salts, rather than N-trityl-imidazoles of the instant type, are disclosed and claimed which also possess superior fungicidal properties.

The present invention also provides a process for the production of the N-trityl-imidazoles of the formula (I) above in which a tritylhalide of the formula (IIa)

in which
R is the same as defined above, and
Hal is a halogen atom, preferably chlorine, is reacted with imidazole (IIb) in a polar inert organic solvent at a temperature of from 0 to 100°C, in the presence of an acid binder.

The term solvent as used herein includes mere diluents

It is decidedly surprising that the specific N-trityl-imidazoles according to the present invention have a considerably stronger fungitoxic activity than the chemically very similar N-trityl-imidazoles previously known. The active compounds according to the present invention therefore represent a valuable enrichment of the art.

The course of the reaction can be illustrated by means of the following reaction mechanism:

(IIb)      (IIaa)      (I₁)

Advantageously, in accordance with the present invention, in the various formulae set forth herein:
R represents
  o-, m- and p- halo, such as chloro, bromo, fluoro or iodo, especially chloro, bromo or fluoro, more especially o-, m- and p- chloro, o-, m- and p- fluoro, and p-bromo; or
  o-, m- and p- nitro, especially p-nitro; or
  o-, m- and p- cyano, especially p-cyano; or
  o-, m- and p- alkyl having 1–3 carbon atoms, such as methyl, ethyl, n- and iso-propyl, and the like, especially o- and p- $C_{1-3}$ alkyl, and particularly o- and p-methyl; or
  o-, m- and p- alkoxy having 1–3 atoms, such as methoxy, ethoxy, n- and iso-propoxy, and the like, especially o- and p- $C_{1-3}$ alkoxy, and particularly o-methoxy; or
  o-, m- and p- alkylmercapto having 1–3 carbon atoms such as methylmercapto, ethylmercapto, n- and iso-propylmercapto, and the like, especially o- and p- $C_{1-3}$ alkylmercapto, and particularly p-methylmercapto; or o-, m- and p- fluoro-substituted alkyl having 1-2 carbon atoms such as methyl, ethyl, and the like, especially fluoro-$C_{1-2}$ alkyl having 1–5 fluoro substituents, more especially mono-, di- and tri- fluoromethyl, and mono-, di-, tri-, tetra-and pentafluoroethyl, and the like, preferably m-fluoro-$C_{1-2}$ alkyl having 1–5 fluoro groups, and particularly m-trifluoromethyl.

Preferably, R is o-, m- or p- chloro, bromo, fluoro, $C_{1-3}$ alkyl, $C_{1-3}$ alkoxy or fluoro-$C_{1-2}$ alkyl having 1–5 fluoro substituents.

In accordance with particular embodiments of the present invention, R is chloro, bromo, fluoro, methyl, methoxy or trifluoro methyl; or p-chloro, bromo or fluoro; or o-methyl or methoxy.

The trityl-halides required as starting materials are clearly characterized by the formula (IIa) above.

Some of these starting trityl-halides are known. The new starting trityl-halides may be prepared in the same manner as the known ones.

Preparation of such starting trityl-halides may be affected as follows: first, the Grignard reagent of the mono-substituted benzene is prepared according to the usual methods. The mono-substituted phenylmagnesium bromide so obtained is then reacted with benzophenone. The organometallic complex compound obtained is subjected to hydrolysis, the appropriate alcohol being formed [compare J. Org. Chem., 7, 392 (1942)].

From the alcohols the chlorides can be obtained simply by reaction with anhydrous hydrogen chloride or with thionyl chloride. The hydroxyl group is replaced by chlorine [compare J. Org. Chem., 7, 392 (1942)].

Of course, the starting imidazole of formula (IIb) above is a well known compound.

According to the present invention, in the reaction of substituted trityl-halides with imidazole, polar inert organic solvents are used as solvents. These include for example, nitriles, such as acetonitrile; sulfoxides, such as dimethylsulfoxide; formamides, such as dimethyl formamide; ketones, such as acetone; ethers, such as diethyl ether; nitroalkanes, such as nitromethane; unsymmetrical hydrocarbons, such as chloroform; and the like. Particularly well suited are polar inert organic solvents which have a dielectric constant of more than 2.4.

The production reaction is carried out in the presence of an acid-binder, i.e. acid-binding agent. Preferably, a suitable excess of imidazole is used. A tertiary amine may, however, also be added, such as triethylamine or dimethylbenzylamine. But the other organic acid-binders customarily employed may also be used.

The reaction temperatures can be varied within a fairly wide range. In general, the work is carried out at substantially between about 0° – 100°C, preferably between about 45° – 90°C.

When carrying out the production process according to the present invention, the starting materials are used in a molar ratio of about 1:1, with about an equimolar amount of acid-binder. The reaction times depend on the reaction temperature and extend from about 3 to 24 hours. When working up, the solvent is removed and the reaction product is freed from amine hydrochloride by washing with water or, if the amine hydrochloride is sparingly soluble in water, it may be separated with an organic solvent.

Advantageously, the particular new active compounds according to the present invention exhibit a strong fungitoxic activity. Because of their low toxicity to warmblooded animals, they are suitable for the control of undesired fungus growth. Their good compatibility with higher plants permits the use of the instant compounds as plant protection agents against fungal plant diseases.

The instant active compounds are particularly suitable for the control of phytopathogenic fungi on above-the-soil parts of plants, as well as against phytopathogenic fungi which attack the plants from the soil.

The instant active compounds exhibit a particularly high fungicidal potency against powdery mildew fungi from the family of the Erysiphaceae, for example against the fungi of the genera Erysiphe, Oidium and Podosphaera; and the like. The active compounds of the present invention may, however, also be used with good results for the control of other phytopathogenic fungi, for example fungi which cause diseases in rice and ornamental plants. The instant active compounds show a good activity against *Piricularia oryzae*, *Pellicularia sasakii* and *Cochliobolus miyabeanus*, three pathogenic agents which occur in rice, and against *Cercospora musae*; and the like. Furthermore, the growth of *Phialosphora cinerescens*, a fungus which attacks carnations from the soil, is also inhibited.

The instant active compounds are distinguished by a high effectiveness in very low concentrations and by a good compatabilty with plants. Doses higher than necessary for the fungicidal effect can therefore be accepted by the plants.

The active compounds according to the instant invention can be utilized, if desired, in the form of the usual formulations or compositions with inert conventional pesticidal diluents or extenders, i.e. inert conventional pesticidal dispersible carrier vehicles, such as solutions, emulsions, suspensions, emulsifiable concentrates, spray powders, pastes, soluble powders, dusting agents, granules, etc. These are prepared in known manner, for instance by extending the active compounds with conventional pesticidal dispersible liquid diluent carriers and/or dispersible solid carriers optionally with the use of carrier vehicle assistants, e.g. conventional pesticidal surface-active agents, including emulsifying agents and/or dispersing agents, whereby, for example, in the case where water is used as diluent, organic solvents may be added as auxiliary solvents. The following may be chiefly considered for use as carrier vehicles for this purpose: inert dispersible liquid diluent carriers including inert organic solvents, such as aromatic hydrocarbons (e.g. benzene, toluene, xylene, etc.), halogenated, especially chlorinated, aromatic hydrocarbons (e.g. chlorobenzenes, etc.), paraffins (e.g. petroleum fractions), chlorinated aliphatic hydrocarbons (e.g. methylene chloride, etc.), alcohols (e.g. methanol, ethanol, propanol, butanol, etc.), amines (e.g. ethanolamine, etc.), ethers, ether-alcohols (e.g. glycol monomethyl ether, etc.), amides (e.g. dimethyl formamide, etc.), sulfoxides (e.g. dimethyl sulfoxide, etc.), ketones (e.g. acetone, etc.), and/or water; as well as inert dispersible finely divided solid carriers, such as ground natural minerals (e.g. kaolins, alumina, silica, chalk, i.e. calcium carbonate, talc, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfonates, aryl sulfonates, etc., and especially alkyl aryl-polyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or herbicides, insecticides, bactericides, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95%, and preferably 0.5–90%, by weight of the mixture, whereas carrier composition mixtures suitable for direct application or field application generally contemplates those in which the active compound is present in an amount substantially between about 0.00001–2%, preferably 0.001–1%, by weight of the mixture. Thus, the present invention contemplates over-all compositions which comprise mixtures of a conventional dispersible carrier vehicle such as (1) a dispersible carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally about 0.00001–95%, and preferably 0.001–95%, by weight of the mixture.

The active compounds can also be used in accordance with the well known ultra-low-volume process with good success, i.e. by applying such compound if normally a liquid, or by applying a liquid composition containing the same, via very effective atomizing equipment in finely divided form, e.g. average particle diameter of from 50–100 microns, or even less, i.e. mist form, for example by airplane crop spraying techniques. Only up to at most about a few liters/hectare are needed, and often amounts only up to about 1 quart/acre, preferably 2–16 fluid ounces/acre, are sufficient. In this process it is possible to use highly concentrated liquid compositions with said liquid carrier vehicles containing 10–80%, preferably 20–60%, or generally from about 20 to about 95% by weight of the active compound, or even the 100% active substance alone, e.g. about 10–100% by weight of the active compound.

In particular, the present invention contemplates methods of selectively killing, combating or controlling fungi, which comprises applying to at least one of (a) such fungi and (b) their habitat, i.e. the locus to be protected, a fungicidally effective or toxic amount of the particular active compound of the invention alone or together with a carrier vehicle as noted above. The instant formulations or compositions are applied in the usual manner, for instance by spraying, atomizing, vaporizing, scattering, dusting, watering, sprinkling, pouring, and the like.

It will be realized, of course, that the concentration of the particular active compound utilized in admixture with the carrier vehicle will depend upon the intended application. Therefore, in special cases, it is possible to go above or below the aforementioned concentration ranges.

The fungicidal effectiveness of the new compounds of the present invention is illustrated, without limitation, by the following examples.

EXAMPLE 1

Podosphaera Test (powdery mildew of apples) [Protective]

Solvent: 4.7 parts by weight acetone
Emulsifier: 0.3 parts by weight alkylaryl polyglycol ether
Water: 95.0 parts by weight The amount of the particular active compound required for the desired concentration of such active compound in the spray liquid is mixed with the stated amount of solvent, and the resulting concentrate is diluted with the stated amount of water which contains the stated emulsifier.

Young apple seedlings in the 4–6 leaf stage are sprayed (treated) with the active compound spray liquid until dripping wet. The plants remain in a greenhouse for 24 hours at 20°C and at a relative atmospheric humidity of 70%. The plants are then inoculated by dusting with conidia of the apple powder mildew causative organism (*Podosphaera leucotricha Salm.*) and placed in a greenhouse at a temperature of 21°–23°C and at a relative atmospheric humidity of about 70%.

10 days after the inoculation, the infestation of the seedlings is determined as a percentage of the untreated but also inoculated control plants.

0% means no infestation; 100% means that the infestation is exactly as great as in the case of the control plants.

The particular active compounds tested, their concentrations and the results obtained can be seen from the following Table 1:

Table 1

| | Podosphaera Test (protective) | | |
|---|---|---|---|
| | Infestation as a percentage of the infestation of the untreated control with a concentration of active compound (in %) of | | |
| Active Compound | 0.0062 | 0.0031 | 0.00156 |
| Known: (A) 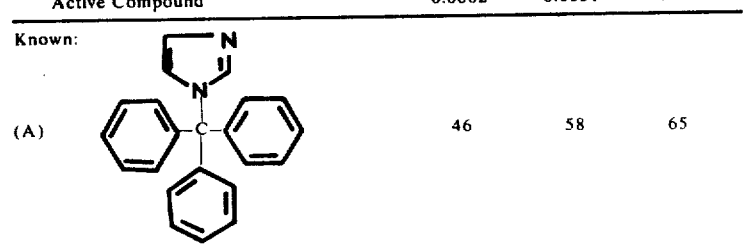 | 46 | 58 | 65 |

Table 1-continued
Podosphaera Test (protective)
| Active Compound | Infestation as a percentage of the infestation of the untreated control with a concentration of active compound (in %) of | | |
|---|---|---|---|
| | 0.0062 | 0.0031 | 0.00156 |
(B) 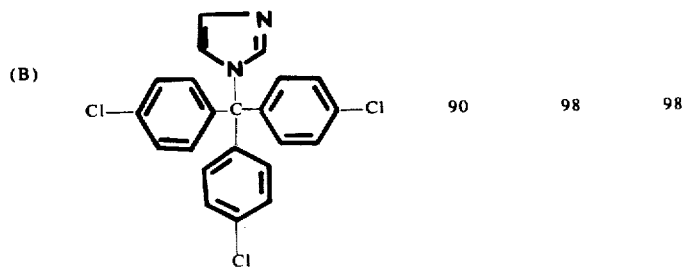 90 98 98
Other compounds tested:
(C) 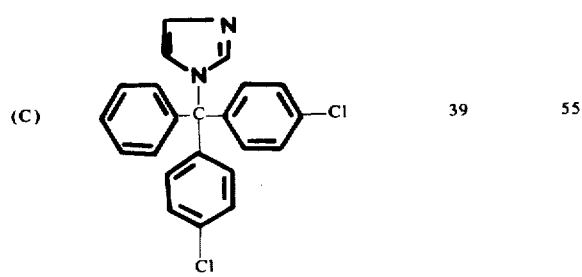 39 55
(D) 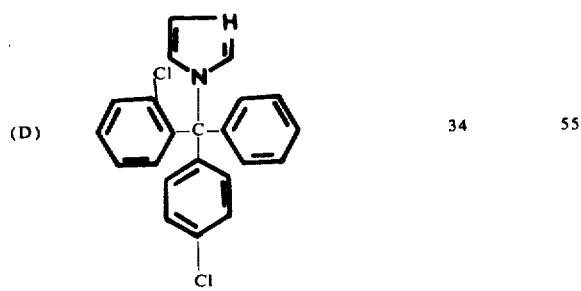 34 55
(E) 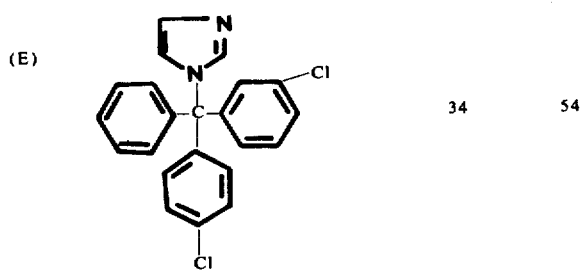 34 54
(F) 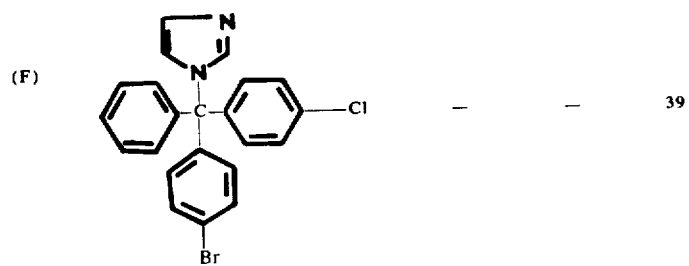 — — 39

Table 1-continued

Podosphaera Test (protective)

| Active Compound | Infestation as a percentage of the infestation of the untreated control with a concentration of active compound (in %) of | | |
|---|---|---|---|
| | 0.0062 | 0.0031 | 0.00156 |

Br

According to the invention:

Active compounds corresponding to formula (I) above in which R has the following meaning:

| | | 0.0062 | 0.0031 | 0.00156 |
|---|---|---|---|---|
| (2₁) | R = p—F | 0 | 14 | 34 |
| (1₂) | R = p—Cl | 5 | 13 | 14 |
| (3₁) | R = o—OCH₃ | 0 | — | 16 |
| (4₁) | R = m—Cl | 0 | — | 1 |
| (5₁) | R = p—Br | 3 | — | 24 |
| (6₁) | R = m—CF₃ | 0 | — | 0 |
| (7₁) | R = o—Cl | 0 | — | 0 |

EXAMPLE 2

A further test was carried out in the same manner as Example 1, with the following results:

Table 2

Podosphaera Test (protective)

| Active Compound | Infestation as a percentage of the infestation of the untreated control with a concentration of active compound (in %) of | | |
|---|---|---|---|
| | 0.0062 | 0.0031 | 0.00156 |
| (8₁) R = o—F | 0 | 0 | 10 |
| (9₁) R = m—F | 0 | 0 | 18 |

EXAMPLE 3

Erysiphe Test
Solvent: 4.7 parts by weight acetone
Emulsifier: 0.3 parts by weight alkylaryl polyglycol ether
Water: 95.0 parts by weight The amount of the particular active compound required for the desired concentration in the spray liquid is mixed with the stated amount of the solvent, and the resulting concentrate is diluted with the stated amount of water containing the stated emulsifier.

Young cucumber plants (Delikatess variety) with about three foliage leaves are sprayed (treated) with the active compound spray liquid until dripping wet. The cucumber plants remain in a greenhouse for 24 hours to dry. The plants are then for the purpose of inoculation, dusted with conidia of the fungus *Erysiphe polyphaga*. The plants are subsequently placed in a greenhouse at 23°–24°C and at a relative atmospheric humidity of about 75%.

After 12 days, the infestation of the cucumber plants is determined as a percentage of the untreated but also inoculated control plants. 0% means no infestation; 100% means that the infestation is exactly as great as in the case of the control plants.

The particular active compounds tested, their concentrations and the results obtained can be seen from the following Table 3:

Table 3

Erysiphe Test

| Active Compound | Infestation as a percentage of the infestation of the untreated control with a concentration of active compound (in %) of | | | |
|---|---|---|---|---|
| | 0.025 | 0.00078 | 0.00019 | 0.00009 |

Known:

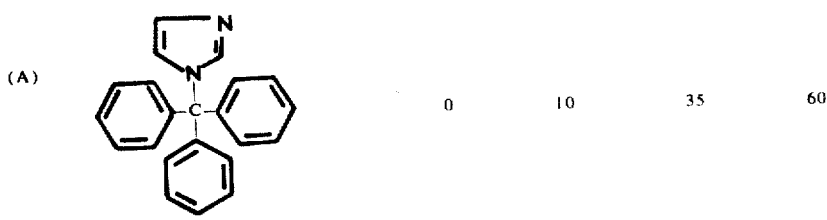

(A)     0     10     35     60

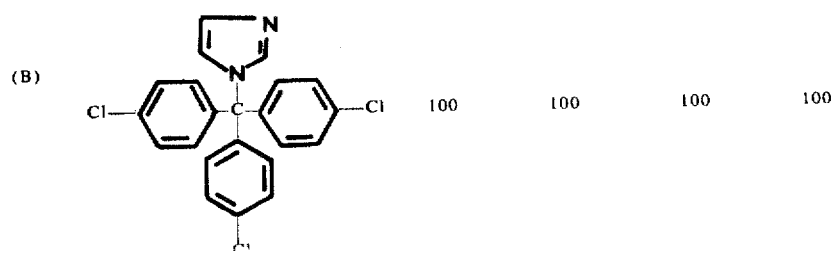

(B)     100     100     100     100

Table 3-continued

Erysiphe Test

| Active Compound | Infestation as a percentage of the infestation of the untreated control with a concentration of active compound (in %) of | | | |
|---|---|---|---|---|
| | 0.025 | 0.00078 | 0.00019 | 0.00009 |

Other compounds tested:

(C) [imidazolyl-C(phenyl)(4-chlorophenyl)(4-chlorophenyl)]    0    7    50    —

(D) [(2-chloro-imidazolyl)-C(phenyl)(phenyl)(4-chlorophenyl)]    0    43    80    —

(E) [imidazolyl-C(phenyl)(2-chlorophenyl)(4-chlorophenyl)]    0    20    50    —

(F) [imidazolyl-C(phenyl)(4-chlorophenyl)(4-bromophenyl)]    0    47    53    —

According to the invention:

Active compounds corresponding to formula (I) above in which R has the following meaning:

| | | 0.025 | 0.00078 | 0.00019 | 0.00009 |
|---|---|---|---|---|---|
| $(2_1)$ | R = p—F | 0 | 0 | 5 | — |
| $(1_1)$ | R = p—Cl | 0 | 0 | 0 | 15 |
| $(10_1)$ | R = p—$CH_3$ | 0 | 0 | — | — |
| $(11_1)$ | R = o—$CH_3$ | 0 | 0 | 13 | — |

Table 3-continued

Erysiphe Test

| Active Compound | | 0.025 | Infestation as a percentage of the infestation of the untreated control with a concentration of active compound (in %) of 0.00078 | 0.00019 | 0.00009 |
|---|---|---|---|---|---|
| (4$_2$) | R = m—Cl | 0 | 0 | 0 | — |
| (6$_2$) | R = m—CF$_3$ | 0 | 0 | 0 | — |
| (7$_2$) | R = o—Cl | 0 | 0 | 0 | — |

EXAMPLE 4

A further test was carried out in a similar manner as Example 3, with the following results:

Table 4

| | Erysiphe Test | | | |
|---|---|---|---|---|
| Active Compound | Infestation as a percentage of the infestation of the untreated control with a concentration of active compound (in %) of | | | |
| | 0.025 | 0.00078 | 0.00019 | 0.00009 |
| (8$_2$) R = o—F | 0 | 0 | 3 | 13 |
| (9$_2$) R = m—F | 0 | 0 | 3 | 10 |

EXAMPLE 5

Mycelium growth Test
Nutrient medium used:
  20 parts by weight agar-agar
  30 parts by weight malt extract
  950 parts by weight distilled water
Proportion of solvent to nutrient medium:
  2 parts by weight acetone
  100 parts by weight agar nutrient medium The amount of the particular active compound required for the desired concentration of such active compound in the nutrient medium is mixed with the stated amount of solvent. The resulting concentrate is thoroughly mixed, in the stated proportion, with the liquid nutrient medium (which has been cooled to 42°C) and is then poured into Petri dishes of 9 cm diameter. Control dishes to which the active compound preparation has not been added are also set up.

When the nutrient medium has cooled and solidified, the dishes are inoculated with the species of fungi stated in the table below and incubated at about 21°C.

Evaluation is carried out after 4–10 days, dependent upon the speed of growth of the fungi. When evaluation is carried out, the radial growth of the mycelium on the treated nutrient media is compared with the growth on the control nutrient media. In the evaluation of the fungus growth, the following characteristic values are used:
  0 no fungus growth
  1 very strong inhibition of growth
  2 medium inhibition of growth
  3 slight inhibition of growth
  4 growth equal to that of untreated control.

The particular active compounds tested, their concentrations and the results obtained can be seen from the following Table 5:

Table 5

Mycelium growth test

| Active Compound | Concentration of Active Compound in ppm | Fungi | | | | |
|---|---|---|---|---|---|---|
| | | Piricularia oryzae | Phialophora cinerescens | Pellucularia sasakii | Cercospora musae | Cochliobolus miyabeanus |
| Known: | | | | | | |

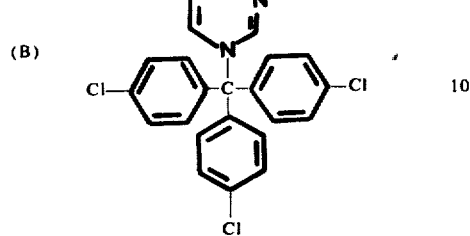

| (B) | 10 | 4 | 4 | 4 | 4 | 4 |

According to the invention:

Active compounds corresponding to formula (1) above in which R has the following meaning:

| (4$_3$) | R = m—Cl | 10 | 0 | 0 | 2 | 0 | 0 |
| (5$_2$) | R = p—Br | 10 | 0 | 0 | 4 | 0 | 1 |
| (6$_3$) | R = m—CF$_3$ | 10 | 0 | 0 | 3 | 0 | 0 |
| (7$_3$) | R = o—Cl | 10 | 0 | 0 | 3 | 0 | 0 |
| (3$_2$) | R = o—OCH$_3$ | 10 | 0 | 0 | 2 | 0 | 0 |
| (1$_4$) | R = p—Cl | 10 | 0 | 0 | 4 | 0 | 0 |

Table 5-continued

Mycelium growth test

| Active Compound | Concentration of Active Compound in ppm | Fungi | | | | |
|---|---|---|---|---|---|---|
| | | Piricularia oryzae | Phialophora cinerescens | Pellucularia sasakii | Cercospora musae | Cochliobolus miyabeanus |
| (2₃)  R = p—F | 10 | 0 | 1 | 2 | 0 | 0 |

The process for producing the particular new compounds of the present invention is illustrated, without limitation, by the following further examples:

EXAMPLE 6

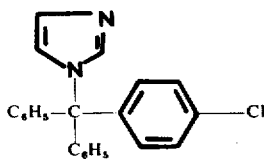
(1₅)

156.5 g (0.5 mol) of (p-chlorophenyl)-(diphenyl)-methyl chloride and 34 g (0.5 mol) imidazole are dissolved in 500 ml acetonitrile, with stirring, and 51 g (0.5 mol) triethylamine are added, whereupon separation of triethylamine hydrochloride occurs even at room temperature. In order to complete the reaction, heating at 50°C is carried out for three hours. After cooling, 1 liter of benzene is added and the reaction mixture is stirred, then washed salt-free with water. The benzene solution is dried over anhydrous sodium sulfate, filtered and concentrated by evaporation; giving 167 g of crude 1-[(p-chlorophenyl)-(bisphenyl)-methyl]-imidazole, m.p. 125°C. By recrystallization from 200 ml benzene and 100 ml ligroin, 115 g (= 71% of the thoery) of pure 1-[(p-chlorophenyl) (bisphenyl)-methyl]-imidazole of m.p. 140°C are obtained.

EXAMPLE 7

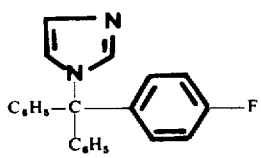
(2₄)

34 g (0.5 mol) imidazole are dissolved at room temperature, with stirring, in a solution of 148.25 g, (0.5 mol) of (p-fluorophenyl)-(diphenyl)-methyl chloride in 500 ml acetonitrile. Following this, 51 g (0.5 mol) triethylamine are added dropwise; triethylamine hydrochloride separates immediately upon heating. For completion of the reaction, the mixture is heated at 50°C for 3 hours. After cooling, the reaction mixture is stirred together with 1 liter of benzene and washed salt-free with water. The benzene solution is dried over anhydrous sodium sulfate, filtered and concentrated by evaporation; giving 148 g of crude 1-[(p-fluorophenyl)-(bisphenyl)-methyl]-imidazole of m.p. 146°C (= 91% of the theory). By recrystallization from 300 ml benzene and 50 ml ligroin, the m.p. rises to 148°C.

The (p-fluorophenyl)-(diphenyl)-methyl chloride used as starting material can be prepared as follows:

174.9 g (1 mol) p-fluoro-bromobenzene in 175 ml ether are slowly added dropwise to 24.3 g (1 gram-atom) magnesium in 300 ml ether. After all the magnesium is dissolved, a solution of 182 g (1 mol) benzophenone in 500 ml ether is added dropwise. The magnesium salt of the alcohol separates from the initially deep-violet solution towards the end of the reaction. By washing with 10% ammonium chloride solution, the alcohol is obtained which, without isolation, is immediately further processed by dissolving it in 1 liter of benzene, adding 50 g of calcium chloride and introducing hydrogen chloride gas until saturation. After filtration and removal of the solvent, the resulting crystal slurry is vigorously suction filtered and the crystals obtained are washed with petroleum ether. 205 g (= 69% of the thoery) of (p-fluorophenyl)-(diphenyl)-methyl chloride of m.p. 88°C are obtained.

EXAMPLE 8

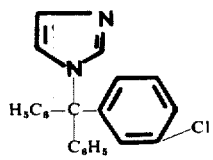
(4₄)

27.2 g (0.4 mol) imidazole and 62.8 g (0.2 mol) of (m-chlorophenyl)-(diphenyl)-methyl chloride are heated to 80°C for 4 hours in 150 ml of dry acetonitrile and 50 ml dimethyl formamide. The solvent is then drawn off and the residue is digested with water to remove the imidazole hydrochloride. The residue is taken up in methylene chloride, dried over sodium sulfate, and the viscous oil remaining behind after the distilling off of the solvent is recrystallized from cyclohexane. 52 g (75% of the theory) of 1-[(m-chlorophenyl)-(bisphenyl)-methyl]-imidazole of m.p. 101°C are obtained.

In analogous manner, the following compounds of the general formula (I) above are prepared:

| Compound | R | m.p. °C |
|---|---|---|
| (7₄) | o—Cl | 140 |
| (6₄) | m—CF₄ | 156 |
| (3₃) | o—OCH₃ | 130 |
| (5₃) | p—Br | 152 |
| (12₁) | p—SCH₃ | 142 |
| (10₃) | p—CH₃ | 130 |
| (8₃) | o—F | 185 |
| (9₃) | m—F | 174 |
| (13₁) | p—NO₂ | 160–170 |
| (14₁) | p—CN | 164 |

It will be realized by the artisan that all of the foregoing compounds contemplated by the present invention possess the desired strong fungicidal properties, with regard to a broad spectrum of activity, as well as a comparatively low toxicity toward warm-blooded creatures and a concomitantly low phytotoxicity, enabling such compounds to be used with correspondingly favorable compatability with warm-blooded creatures and plants for more effective control and/or elimination of fungi by application of such compounds to such fungi and/or their habitat.

It will be appreciated that the instant specification and examples are set forth by way of illustration and not limitation, and that various modifications and changes may be made without departing from the spirit and scope of the present invention.

What is claimed is:

1. An antifungal composition useful against fungal plant diseases which comprises antifungal effective amount of a compound of the formula:

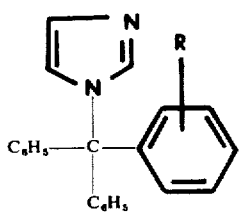

wherein R is o-methyl, p-methyl, o-ethyl, or o-isopropyl, in combination with a solid or liquid diluent or carrier.

2. An antifungal composition according to claim 1 in the form of a solution.

3. An antifungal composition according to claim 1 in the form of an emulsion.

4. An antifungal composition according to claim 1 in the form of a suspension.

5. An antifungal composition according to claim 1 in the form of a powder.

6. An antifungal composition according to claim 1, wherein the compound is present in an amount substantially between about 0.00001 to 95%.

7. An antifungal composition according to claim 1, wherein R is p-methyl.

8. A method for controlling fungal diseases in plants which comprises applying to the fungi or to the plant to be protected an antifungal effective amount of a compound of the formula:

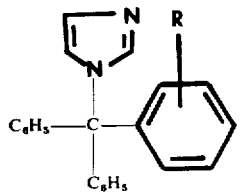

wherein R is methyl, o-ethyl or o-isopropyl.

9. A method according to claim 8, wherein the application is by spraying.

10. A method according to claim 8, wherein the application is by scattering the compound on the fungi or plant to be protected.

11. A method according to claim 8, wherein the application is by dusting the compound on the fungi or plant to be protected.

12. A method according to claim 8, wherein R is o-methyl or p-methyl.

13. A method according to claim 8, wherein R is o-methyl.

14. A method according to claim 8, wherein R is p-methyl.

* * * * *

UNITED STATES PATENT OFFICE
CERTIFICATE OF CORRECTION

PATENT NO. : 3,934,022
DATED : January 20, 1976
INVENTOR(S) : Karl Heinz Buchel et al It is certified that error appears in the above-identified patent and that said Letters Patent are hereby corrected as shown below:

Column 1, the first structural formula should read:

-- 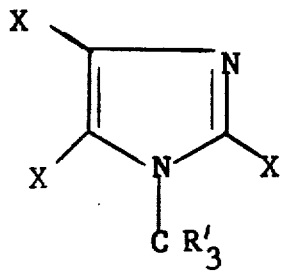 --.

Signed and Sealed this thirteenth Day of April 1976

[SEAL]

Attest:

RUTH C. MASON
*Attesting Officer*

C. MARSHALL DANN
*Commissioner of Patents and Trademarks*